United States Patent [19] [11] Patent Number: 4,496,971
West et al. [45] Date of Patent: Jan. 29, 1985

[54] DETECTION APPARATUS

[75] Inventors: Geoffrey A. W. West, London; Leonard Norton-Wayne, Glenfield, both of England

[73] Assignee: National Research Development Corporation, London, England

[21] Appl. No.: 398,880

[22] Filed: Jul. 16, 1982

[30] Foreign Application Priority Data

Jul. 22, 1981 [GB] United Kingdom ............... 8122618

[51] Int. Cl.³ .............................................. H04N 7/18
[52] U.S. Cl. .................................... 358/106; 356/394; 358/101; 358/107; 364/507; 382/8
[58] Field of Search ................ 358/106, 107; 364/507; 356/394; 382/8

[56] References Cited

U.S. PATENT DOCUMENTS

| 3,887,762 | 6/1975 | Uno | 358/106 |
| 4,152,723 | 5/1979 | McMahon | 358/106 |
| 4,349,880 | 9/1982 | Southgate | 358/106 |
| 4,378,494 | 3/1983 | Miller | 358/106 |
| 4,379,308 | 4/1983 | Kosmowski | 358/106 |

Primary Examiner—Howard W. Britton
Attorney, Agent, or Firm—Cushman, Darby & Cushman

[57] ABSTRACT

Printed circuits can be inspected by eye, which is fatiguing or automatically by comparison with a master pattern by optical super-imposition, which requires great precision in handling. In the present invention analysis of optical scanning of a pattern determines the directions of boundaries of features of the pattern and employs this analysis to identify any local divergence from the prevailing direction of the boundary.

14 Claims, 23 Drawing Figures

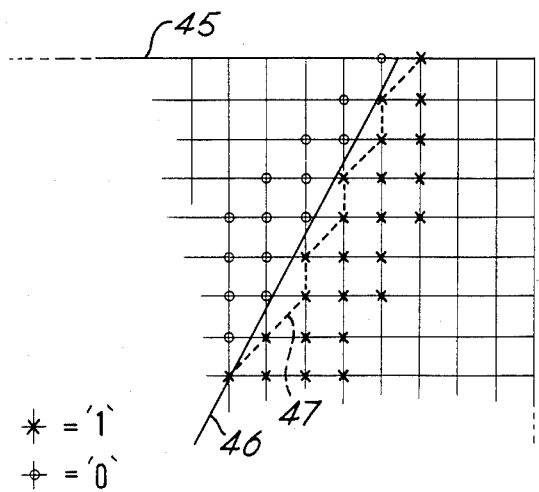
* = '1'
+ = '0'
Fig. 4
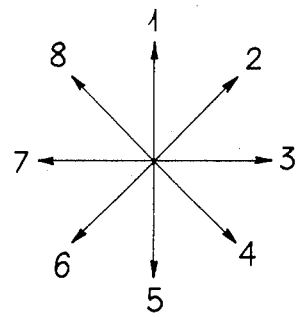
Fig. 5a
Fig. 5b
| CODE | 1 | | 2 | | 3 | | 4 | | 5 | | 6 | | 7 | | 8 | |
|---|---|---|---|---|---|---|---|---|---|---|---|---|---|---|---|---|
| MASKS M1-M8 | 0 | 1 | 0 | 1 | 0 | 0 | 1 | 0 | 1 | 0 | 1 | 1 | 1 | 1 | 1 | 1 |
| | 0 | 1 | 1 | 1 | 1 | 1 | 1 | 1 | 1 | 0 | 1 | 0 | 0 | 0 | 0 | 1 |

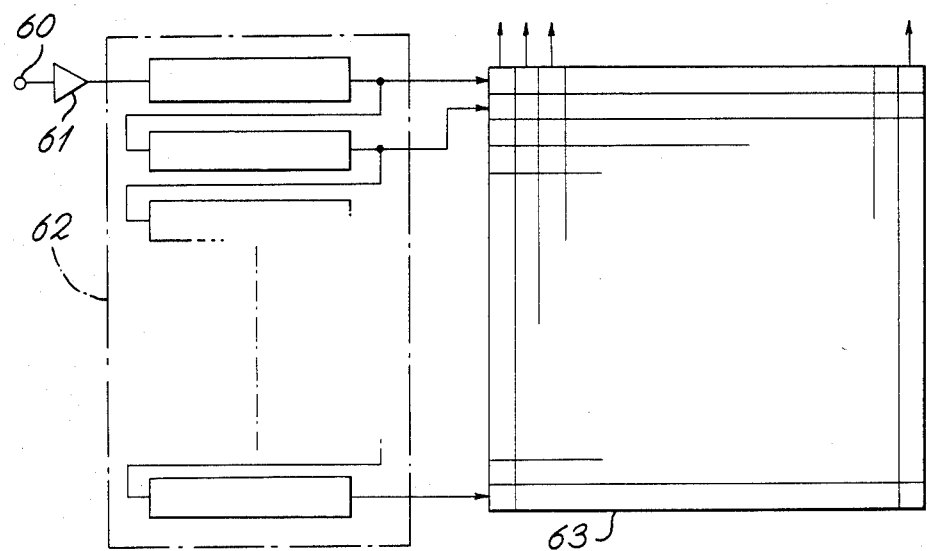
Fig. 6
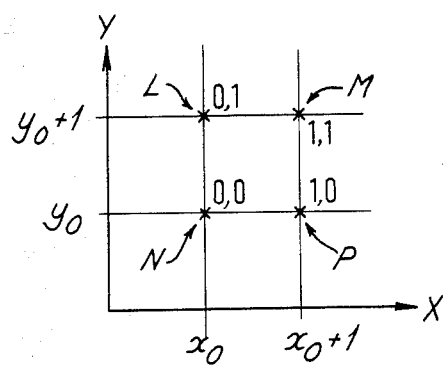
Fig. 8a
| MASK | COORDINATES | | | |
|------|-------------|---|---|---|
| | START | | FINISH | |
| | X | Y | X | Y |
| M1 | 1 | 0 | 1 | 1 |
| M2 | 0 | 0 | 1 | 1 |
| M3 | 0 | 0 | 1 | 0 |
| M4 | 0 | 1 | 1 | 0 |
| M5 | 0 | 1 | 0 | 0 |
| M6 | 1 | 1 | 0 | 0 |
| M7 | 1 | 1 | 0 | 1 |
| M8 | 1 | 0 | 0 | 1 |
Fig. 8b

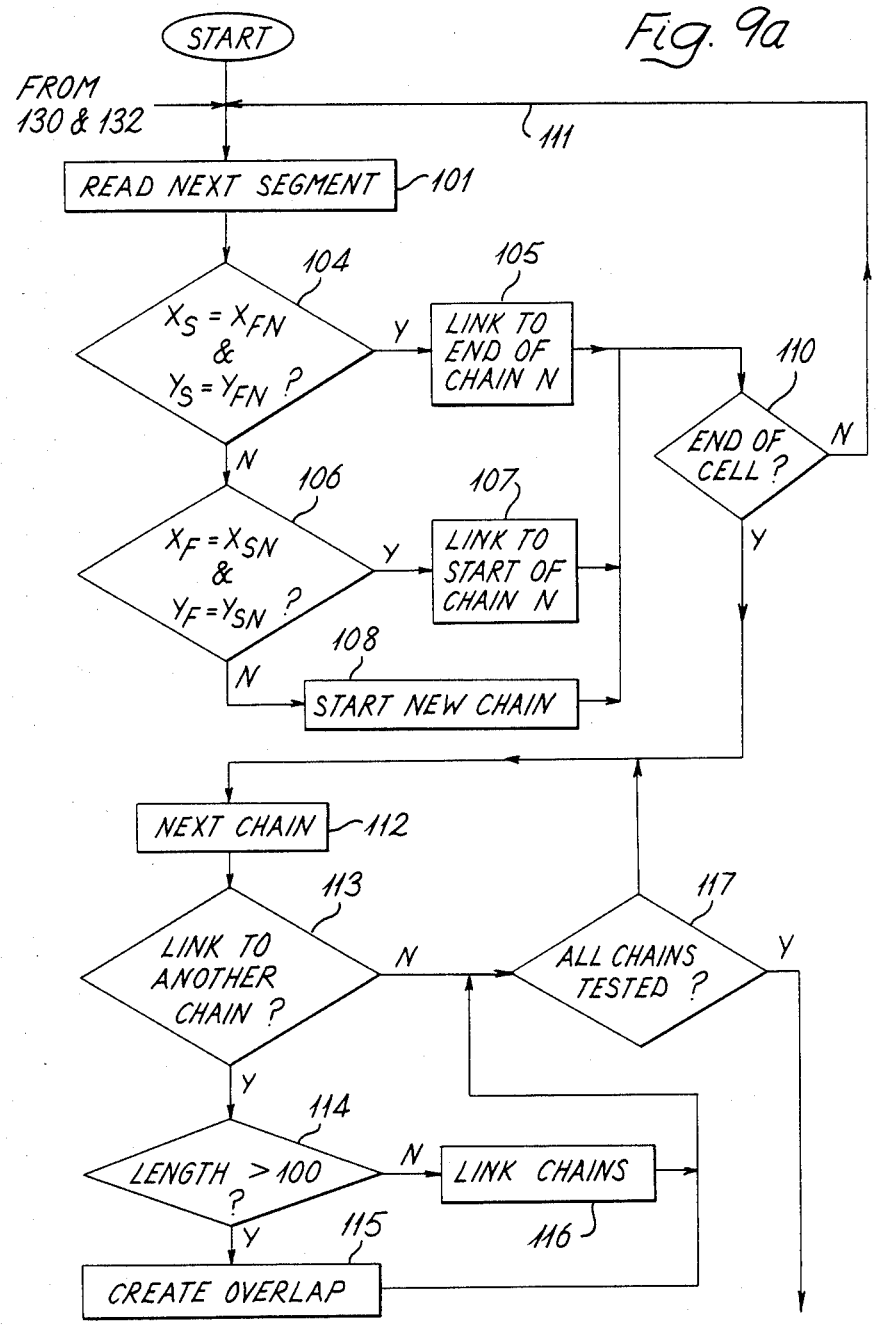

DETECTION APPARATUS

The invention relates to a method and apparatus for the detection of anomalies in the reproduction of a pattern, particularly a printed circuit.

The scale of construction and the close spacing of the printed features of a patterned device such as a printed circuit for an electronic device are such as to create difficulty in inspection. Visual inspection is fatiguing and comparison with a master pattern, for example by some form of optical super-imposition, requires great precision in handling. At the same time the kind of minute anomaly or defect in the pattern which can render the circuit useless or dangerous in operation if undetected is usually quite readily identifiable as a departure from the regularity of the structure. It is intended therefore that a pattern to which the invention may be applied will be one having known rules of geometrical construction, a breach of which is identifiable without reference to a master pattern.

According to the first aspect of the present invention there is provided a method of detecting anomalies in a reproduction of a pattern on a workpiece comprises the operation of irradiating that surface of the workpiece carrying the pattern, scanning the said surface with detection means sensitive to such radiation to derive a video signal representing an array of points on the said surface, the signal having at least two levels relating to respective features of the pattern, deriving a digital value of the signal for each point, comparing each such value with a predetermined threshold value to determine those points which constitute a first feature of the pattern, determining those points which define a boundary of the first feature, determining changes of direction between successive points on the boundary, and identifying any anomaly in the boundary which has at least one dimension which is comparable to the smallest dimension of the pattern.

The radiation may be reflected to derive the video signal, different features of the pattern having distinctive values of reflectance.

A preliminary identification of such divergence may be made if the length of the boundary extending between two points is large compared with the direct distance between the points.

The comparison may be made for pairs of points at progressively displaced positions on the boundary, each pair of points being separated by an equal number of boundary elements.

A confirmatory identification of such divergence may be made if the sequence of changes of direction includes two changes in the same sense separated by at least one change of the opposite sense.

The characteristics of the reproduction of the pattern are established entirely in terms of internal relationships derived from observation of the features of the reproduction. In particular the orientation of the workpiece is not predetermined. It is necessary to know sufficient of the general nature of the pattern and the inspection criteria to be applied to enable a suitable scale of dimension to be established for assessment of the divergent features.

The sequence of operations defined above may be used for the detection of small-scale faults in a workpiece following a visual examination for larger scale faults.

Alternatively the final steps of the sequence may be preceded by an imaging procedure for detecting large-scale faults, in which data from the workpiece is related to a predetermined orientation to enable the values of parameters derived for each elemental area of the said surface to be compared with values for corresponding elemental areas of a master pattern, the parameters being the perimeter of the first feature of the pattern and the area of the feature.

The sequences for detecting small-scale faults and large-scale faults derive from a common stage of image data collection and together may form a continuous procedure. The range of sensitivity of each sequence may be related to the other so that no fault of intermediate scale is undetected.

In accordance with a second aspect of the invention there is provided apparatus for detecting anomalies in a reproduction of a pattern on the surface of a workpiece comprising means for irradiating the said surface such that at least two different levels of reflectance relate to respective features of the pattern, means responsive to such reflected radiation for scanning the said surface to derive a video signal representing the reflectance at each of an array of points on the surface, means for deriving a digital value of the signal for each point, means for comparing each value with a predetermined threshold value to determine those points which represent a first feature of the pattern, means for identifying those points which define boundaries of the first feature, means for deriving the directions of the boundaries between points, and means for analysing the said directions to indicate the presence of anomalies in the boundaries which have at least one dimension which is comparable to the smallest dimension of the pattern.

The invention will be further explained and by way of example an apparatus and procedure for carrying out the invention will be described with reference to the accompanying drawings in which:

FIG. 2(a) represents a possible fault to be detected in the circuit of FIG. 1 in the form of a gap in a track;

FIG. 2(b) represents a possible fault to be detected in the circuit of FIG. 1 in the form of a notch and an outcrop;

FIG. 2(c) represents a possible fault to be detected in the circuit of FIG. 1 in the form of a nick in a track;

FIG. 2(d) represents a possible fault to be detected in the circuit of FIG. 1 in the form of a narrow longitudinal defect in a track;

FIG. 2(e) represents a possible fault to be detected in the circuit of FIG. 1 in the form of a hairline crack in a track;

FIG. 2(f) represents a possible fault to be detected in the circuit of FIG. 1 in the form of a spur extending between two tracks;

FIG. 4 represents an array of binary values corresponding to a portion of a printed circuit imaged by the system of FIG. 3;

FIG. 5(a) illustrates the direction coding used in coding boundary elements;

FIG. 5(b) is a table giving the masks used in coding boundary elements and which correspond with the codes of FIG. 5(a);

FIG. 6 represents schematically a circuit for the initial processing of data input from the system of FIG. 3;

FIG. 8(a) illustrates a convention for handling coordinate data representing an element of a boudnary;

FIG. 8(b) is a table of the start and finish points for boundary elements matching various masks;

FIG. 9a is a flow chart for deriving chain codes representing boundaries.

Figure 1:
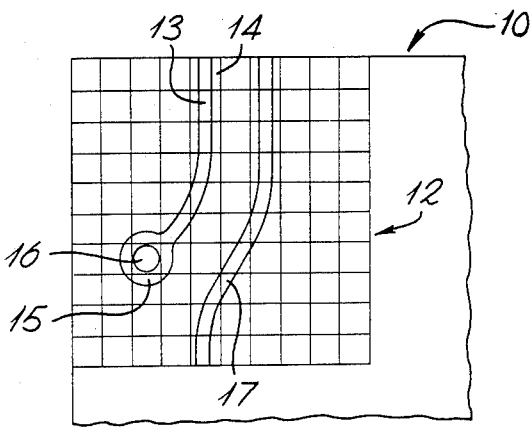
FIG. 1 represents a portion of a printed circuit.
Figure 2:
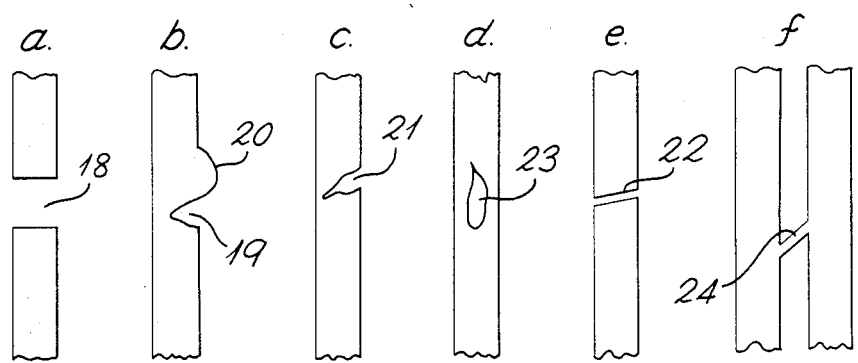
FIG. 2 represents possible faults to be detected.

In applying the invention to the inspection of printed circuits the nature of the problem to be solved is indicated in FIGS. 1 and 2. A sample area 2 cm square of a printed circuit board 10 is shown in FIG. 1 with a superimposed grid 12 of 2 mm squares. A conductive track 13 enters the sample area at a square 14 and terminates on a pad 15 for connection below the board via a thru-plated hole 16. Other tracks such as a track 17 pass through the sample area and in general the tracks cannot be assumed to be either straight or parallel to each other for any extended distance. The track width in this example is about 1 mm and the minimum separation between tracks is of similar size. Visually, the tracks are distinguishable by a high value of reflectance from the insulating surface of the board which forms a relatively non-reflective background. Inspection may be carried out at various stages in production, for example shortly after the etched copper substrate of the board has been flow-coated with solder or where blue etch resist has been applied to the board, or may be carried out on delivery to a buyer.

FIG. 2 shows sections of track with a range of defects. In (a) and (b) are shown defects which will be referred to in this specification as 'large-scale' and are characterized by dimensions of trackwidth or a substantial fraction of trackwidth in two directions. Such defects, in (a) a gap 18 in the track and in (b) a notch 19 and an outcrop 20, can be detected in a preliminary stage of inspection either by eye or by electronic imaging. Other large-scale faults include missing pads and tracks and large superfluous areas of solder. Track sections (c) to (f) show defects which will be referred to in this specification as 'small-scale', the intended distinction being that at least in one direction the defect extends for a distance which is small relative to track-width. In section (c) a narrow nick 21 extends part way across the track; in (e) the track is broken by a hairline crack 22; in (d) a narrow longitudinal defect 23 lies within the track; and in (f) a narrow spur or bridge 24 extends between two tracks. The detection of such small-scale defects is the principal subject of the present invention and involves the investigation of the track boundary to determine the presence of anomalies typified by the re-entrant divergence of the nick 21 or the salient divergence of the spur 24 from the prevailing direction. A small-scale defect is in general readily identifiable as an anomaly because it represents a relatively large and abrupt change in direction on a boundary which otherwise changes slowly over a short distance if it is curved or shows no change if it is straight. By contrast, a large-scale defect often cannot be distinguished from a design feature except by comparison with the master pattern.

Figure 3:
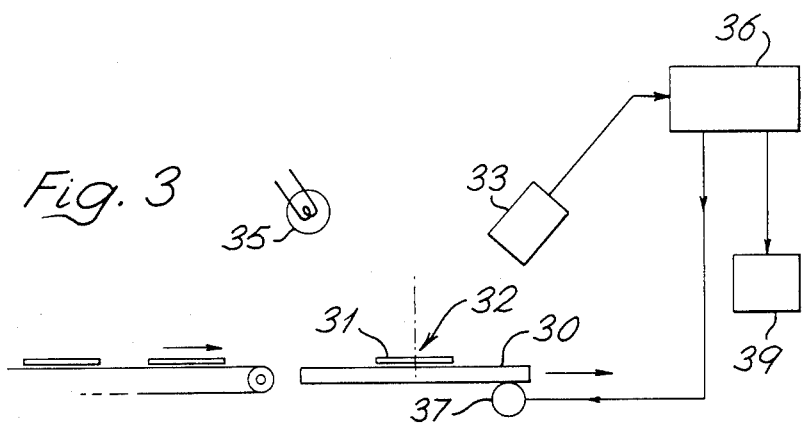
FIG. 3 represents schematically an inspection system suitable for operation in accordance with the method of the invention.

Referring now to FIG. 3, a generally schematic illustration of an inspection apparatus includes a movable table 30 on which printed circuit boards such as a board 31 are presented in sequence for inspection. An inspection axis 32 transverse to the direction of motion of table 30 is defined by a line-scan camera 33 mounted above the table. Camera 33 comprises a linear array of photosensitive charge-coupled devices and an optical focusing system which enables adjacent points along axis 32 to be resolved at a spacing of, for example, less than 50 $\mu$m. It will be assumed that for the observation of tracks of 1 mm width, dissection into elements one-tenth of this width (i.e. 100 $\mu$m) is sufficient; any possible analytical advantage in improving the resolution must be weighed against the increased data handling capacity and time but the requirements of each application must be considered. Board 31 is illuminated as uniformly as possible from a source 35 and the varying levels of reflected light along axis 32 are sensed by the camera 33. The output level of each element of the camera array is received by a schematically indicated unit 36 which embraces the digitization, storage, computation and control facilities for the generation and processing of imaging data. As soon as complete data for the first scan line has been received, a control signal is produced by unit 36 to cause a stepping motor 37 to operate to advance table 30 by 100 $\mu$m. A second scan-line is then produced and the area of the board is thus progressively imaged in elemental areas 100 $\mu$m square. The inspection unit may be continuously supervised by an operator, the unit 36 having an associated display 39 on which the board is represented and any defects are traced as they are detected so that the operator can immediately judge whether to withdraw the board for correction. Alternatively a defective board may be identified for automatic diversion into a 'reject' stream at the end of table 30, a coded reference to the nature and location of the defect being printed out by unit 36.

The image processing operation of unit 36 will first be described functionally since it will be appreciated that most of the detailed steps involved can be carried out either in software or in hardware and that those skilled in the art will be able to provide the required facilities. Specific reference will later be made to hardware where a preference arises, for example in achieving a satisfactory speed of operation.

The detection of large scale defects requires comparison with a master pattern both in area and perimeter. It will be noted by reference to FIG. 2b that two defects 19 and 20 may give the true area when added but that a large cumulative error in perimeter results. To collect data for the master pattern a printed cicruit board known to be of good quality is passed under camera 33 in a known orientation and an analogue signal representing brightness in each elemental area is input to unit 36. In some conditions the dark level of the substrate appears relatively uniform while the track brightness varies substantially. The two features are distinguished by dilitization of the analogue values on an 8-bit scale, preparing a histogram of the digital values, identifying the low-level peak which represents substrate reflection and setting a threshold at a level which excludes the whole of that peak. All higher values are assumed to result from reflection from a track and are represented by the storage of '1's at addresses corresponding to the scan position from which the value originated. Substrate elements are similarly represented by '0's. The stored values are then reviewed in blocks corresponding to sub-divisions of the area of the board, which will be termed 'cells'. Thus each of the squares 12 in FIG. 1 is one such cell, each cell in the present embodiment containing 20×20 elements. It will be appreciated that to avoid possible ambiguity at adjoining edges, 21 elements are taken into account, so allowing an overlap with the preceding cell. FIG. 4 indicates part of a cell 45 in which an edge 46 of a track runs diagonally across the cell and elements of the cell near the edge 46 are marked to indicate the stored value '1' or '0' for that element. For the purpose of the diagram in FIG. 4 each intersection in the grid of lines represents the centre of an element and the values '0' and '1' are indicated by '0' and 'X'. Cell 45 can be characterized by the area of the track within it and by the length of the track perimeter. Area is simply represented by the total number of '1's. Evaluation of the perimeter requires the position and direction of the track edge to be determined and this is done by comparing successive sets of four stored values with each of a set of four-element masks as follows:

When a match is found with a mask:

| 1 | 0 | or | 0 | 1 |
|---|---|----|---|---|
| 1 | 0 |    | 0 | 1 | a vertical boundary must be present. Similarly a horizontal boundary must give a match with masks:

| 0 | 0 | or | 1 | 1 |
|---|---|----|---|---|
| 1 | 1 |    | 0 | 0 | and a diagonal boundary with masks:

| 0 | 1, | 1 | 0, | 1 | 1, | 1 | 1 |
|---|----|---|----|---|----|---|---|
| 1 | 1, | 1 | 1, | 1 | 0, | 0 | 1 |

In FIG. 4 a broken line 47 shows the boundary elements derived by masking in this way. The perimeter length for each element of horizontal or vertical boundary is simply the element size, 100 μm, and the length for each diagonal element is $\sqrt{2} \times 100$ μm. The element lengths thus determined are summed to give a total length of reasonable accuracy. There is some uncertainty when the boundary crosses an element of the cell whether that element will be recorded as '1' or '0' and thus whether it will be interpreted as a step or a diagonal. Any cumulative over- or under-estimate is unlikely and this kind of quantizing error may be expected to affect the estimates for the test board and the master pattern similarly.

Having established reference values of track area and perimeter length for each cell of the master pattern, each test board is examined in the same way and values compared cell by cell. The cell area is small and therefore any significant error in the track plating or boundary will appear relatively large. The sensitivity to error is thus much greater than if a similar comparison were to be made over the board in total. The test board should be presented in the same orientation as the master. Alternatively table 30 can be made rotatable to produce the required orientation in response to a signal derived from such alignment identification features.

In proceeding to search for small-scale faults the elemental '1', '0' data derived during the large-scale search is further processed. Depending on the time required for these operations the test board may be retained at the inspection position or transferred to a holding position to permit scanning data to be acquired from the next test board.

Figure 5C:
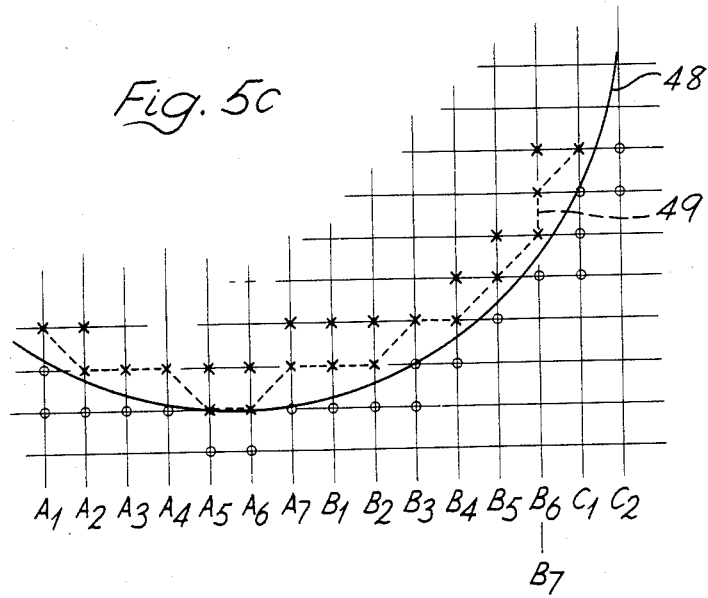
FIG. 5(c) illustrates the edge of a track and a boundary developed in forming a coded representation of the edge.

The small-scale fault detection procedure is carried out in either one or two stages. A first stage is conclusive if no fault is indicated; if a fault is indicated, the indication may be true or false and a second stage is necessary to distinguish between these possibilities. The situation can arise because, although the initial fault test criterion is always validly applied, it may be satisfied by some boundary profiles which are correct. The first stage commences by tracing a boundary within the first cell in which a track appears. A mask sequence is applied as before to determine direction but for the present purpose the direction of each boundary element is coded according to the key shown in FIG. 5(a). Starting from North (coded 1), NE is coded 2 and so on in 45° steps up to code 8. A sequence of such code numbers representing successive directional changes along a boundary is known as a Freeman chain code. In applying the masks a fixed convention must of course be adopted in coding the two directions on each axis, for example to distinguish a vertical boundary as '1' or '5'. The convention to be applied in the present discussion is illustrated in FIG. 5(b) in which masks M1 to M8 are shown in correspondence with codes 1 to 8. An application of the convention is shown for a portion of track boundary in FIG. 5(c).

The principle adopted in the first stage of small-scale fault detection is that a boundary may be assumed substantially unchanging in direction over a distance which is comparable to the smallest known feature of the pattern. Assuming this distance to be 1 mm, equal to the track width, the change in boundary direction has been assessed on the chain coding of seven boundary elements which cover a maximum (diagonal) distance of almost 1 mm or a minimum distance of 0.7 mm. Referring to FIG. 5(c) a portion of track bounded by an arc 48 of 1 mm radius and lying within one cell is chain coded in correspondence with the quantized boundary 49. From a point $A_1$, the boundary 49 is developed initially as far as a point $B_1$, through seven elements by way of points $A_2$ to $A_7$. At each step the distance travelled and the new coordinates can be derived.

| Element | Chain code | Distance $\sqrt{2}$ | Distance 1 | Coordinate change X | Coordinate change Y |
|---|---|---|---|---|---|
| | | | | $A_1$  0 | 0 |
| $A_1A_2$ | 8 | $\checkmark$ | | $A_2$  +1 | −1 |
| $A_2A_3$ | 7 | | $\checkmark$ | $A_3$  +1 | 0 |
| $A_3A_4$ | 7 | | $\checkmark$ | $A_4$  +1 | 0 |
| $A_4A_5$ | 8 | $\checkmark$ | | $A_5$  +1 | −1 |
| $A_5A_6$ | 7 | | $\checkmark$ | $A_6$  +1 | 0 |
| $A_6A_7$ | 6 | $\checkmark$ | | $A_7$  +1 | +1 |
| $A_7B_1$ | 7 | | $\checkmark$ | $B_1$  +1 | 0 |
| | | 4.24 | 4 | +7 | −1 |

The distance $A_1B_1$ along boundary 49 is thus 8.24 and the direct distance between the coordinates (0.0) and (+7, −1) is 7.07. A deviation of 1.17 elements (i.e. 117 μm) is computed in unit 36 for comparison with a threshold level which is set according to the desired severity of inspection. The value of deviation carries no information about the actual shape of the boundary and the value 1.17, derived on the present example from an arc of a true circle, might equally represent an actual error in a straight edge. If such an error must be detected the threshold will be set accordingly. The error will then always be found but some false alarms, such as the designation of the circular arc as faulty, will also occur. The procedure continues by carrying out the same calculation on boundary 49 for paths $A_2B_2$, $A_3B_3$ . . . in succession. No further information is obtained about the circular arc 48 in this way, but for a boundary which includes as a defect an abrupt change in direction, a significant advantage is obtained by considering successive overlapping portions of the boundary. It will be apparent that a sharp bend which occurs near one end of a chain of such elements may show no significant deviation. However, when the point of observation has advanced so that the bend lies at the centre of the chain, the measured deviation is enhanced.

Figure 5D:
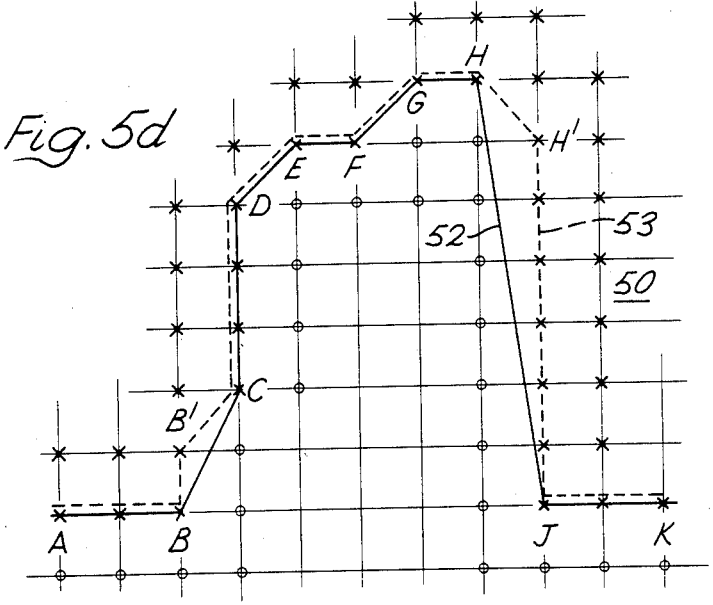
FIG. 5(d) illustrates a procedure for detecting a portion of a defect in a track.

As a result therefore of the first stage of the small-scale detection procedure, the presence of all apparently anomalous boundary features is detected but it is not known which of them in fact represent defects. The approximate location is known, however, and in the second stage the locations are re-examined. Essentially the directional information obtained by chain coding the first stage is further processed to determine the distance over which each change of direction persists. The procedure will be followed with reference to FIG. 5(d) for a defect in a portion of a track 50 in the form of a re-entrant boundary 52 in which the directional change points are indicated by the letters AB . . . K. By masking, a quantized boundary 53 is derived (indicated as a broken line) in which directional change points which depart from boundary 52 are indicated at B' and H'. It can be seen that on applying the first stage procedure, the seven elements from A to D have a boundary length of 7.4 while the direct distance from A to D is about 5.8. For a threshold deviation of less than 1.6 a fault will have been indicated in this region.

Now applying the second stage procedure, the chain coding for boundary 53 is first listed as in column 2 of the following table (TABLE I). In column 3 the changes in direction of the track are denoted by a so-called curvature code in which the differences between the chain codings of the successive elements are recorded.

TABLE 1

| Element | Chain code | Curvature code (change of direction from preceding chain coding) |
|---|---|---|
| AB | 7 | |
| | 7 | 0 |
| BC (BB') | 5 | −2 |
| (B'C) | 6 | 1 |
| CD | 5 | −1 |
| | 5 | 0 |
| | 5 | 0 |
| DE | 6 | 1 |
| EF | 7 | 1 |
| FG | 6 | −1 |
| GH | 7 | 1 |
| HJ (HH') | 8 | 1 |
| (H'J) | 1 | 1 |
| | 1 | 0 |
| | 1 | 0 |
| | 1 | 0 |
| | 1 | 0 |
| | 1 | 0 |
| | 7 | −2 |
| JK | 7 | 0 |

The curvature coding data are subject to further reduction but it is clear that a step of two in the chain code (i.e. the appearance of ±2 in the curvature code) indicates a right-angled bend and that the sign indicates the direction of the bend. The pattern of such signs is indicative of the nature of the deviation of the boundary as will appear from the simple manipulation of curvature code data in the following table (TABLE II). Column 1 contains the curvature codes from TABLE I and the entries in the other columns will be explained.

TABLE II

| Curvature code | Changes in direction | Duration | Turning points | Distance |
|---|---|---|---|---|
| 0 | 0 | 1 | | |
| −2 | −2 | 1 | −2(B) | 2.0 |
| 1 | 1 | 1 | | |
| −1 | −1 | (0) 1 | (2) | |
| 0 | | | | |
| 0 | 0 | 2 | | |
| 1 | | | | |
| 1 | 2 | 2 | 2(DE) | 7.5 |
| −1 | −1 | 1 | −1(F) | 9 |
| 1 | | | | |
| 1 | | | | |
| 1 | 3 | 3 | 3(GHH') | 11 |
| 0 | | | | |
| 0 | | | | |
| 0 | | | | |
| 0 | | | | |
| 0 | 0 | 5 | | |
| −2 | −2 | 1 | −2(J) | 18 |
| 0 | 0 | 1 | | |

In the second column a summary of the curvature code is prepared by entering either the result of a single step if it is not repeated of the cumulative result for any succession of similar steps. The third column records the number of steps in each case. Any sequence of changes of direction which represent noise are then re-written as is described below with reference to Table III, one such sequence being shown in Table II where re-written values are shown in brackets. Since the purpose is to identify suspected anomalies in the pattern as indicated by 45° turns, or any sharper turn, a threshold of value '1' is applied to the values in column two. Column four then shows five positions at which the threshold is passed and by accumulating sub-totals from column three the distance of each position from the starting point of the chain can be derived, as in column five. The value −2 at positions (B) and (J) signifies a re-entrant divergence from the boundary and the value +2 at positions which are taken by averaging to be centred on the segments (DE) and (GHH') signifies the end of the re-entrant. Comparison of the distances in column 5 of TABLE II shows first that the indirect distance BJ=16 units is much greater than the direct distance which can be measured as equal to 6 units so that a defect is probable. Values for the depth and internal width of the re-entrant are then obtained from column 5: (B)−(DE)=5.5; (DE)−(GHH')=3.5; (GHH')−(J)=7. All of these dimensions are significantly greater than one unit and in relation to the width of the track (10 units) represent a substantial defect.

The pattern of direction changes indicated in column 4 of TABLE II may be denoted by the sign-sequence −*+*+*− where * indicates the possible occurrence of a sign which may be of either type (for values at or above a threshold 1) and a corresponding salient divergence from the boundary would give the sequence +*−*−*+. A different shape of defect such as a wedge may have only a single internal turning point and the sequences −*+*− or +*−*+ will result. Such four corner and three corner faults are similar to the faults shown in FIG. 2(c). Two corner faults also occur for example at track breaks and shorts (see FIGS. 2(e) and 2(f)). Subject to satisfaction of the dimensional relationships all of the four sequences are valid indications of a defect.

In summary, a fault is positively identified by the presence together of the factors:

(a) sign sequence (b) between the positions of the outer sign changes of the sequence the direct distance is much less than the distance round the boundary (c) the depth of the deviation exceeds a value prescribed for the specific workpiece.

To return to the problem illustrated in FIG. 5(c) of the possible misinterpretation of a circular arc as a track defect, it will now be apparent that the circle will nowhere show the dimension necessary to satisfy criteria (b) and (c). The second stage of the detection procedure has therefore eliminated this source of false alarms.

The application of chain coding in the detection of small-scale defects is subject to some limitations. First, adjacent boundary portions of a defect, such as the parallel sides of a slot, must be larger than the element size determined by the resolution of the imaging system. In the embodiment described the smallest gap which could be identified in a chain code would be at least 100 µm, i.e. a value greater than the width of a picture element. Second, the detection procedure for re-entrant or other defects may not be informative or may mislead if the chain is too short. Chain codes are extended until at least forty segments are included by scanning and coding across the array of cells 12 (FIG. 1), joining chains in adjacent cells where they represent the same boundary. For economy in time and in storage capacity data for only small areas of the pattern are retained in a storage, device and chain codes are almost completely erased when the detection procedure relevant to them has been completed. Continuity across cell boundaries is preserved by holding the last ten segments of any chain which is capable of extension into an adjoining cell.

In considering the operation of unit 36 of FIG. 3 the implementation of the principal functions in hardware will be described. It will be apparent that large amounts of data need only be handled at the initial input stage and that once the picture elements which define boundaries have been identified, the data representing unbroken areas of substrate or of track are of no interest. Referring to FIG. 6, an input point 60 receives in sequence the analogue video signal from each of the sensors of camera 33. The signal is compared with a predetermined threshold value at a comparator 61 which produces an output '1' whenever the threshold is exceeded and a '0' whenever the input is below threshold level. The binary output from comparator 61 is stored in a shift register 62 having a capacity of twenty-one scan lines each containing (say) 1001 points. For 100 µm resolution such a line covers a board 10 cm wide which is divided for processing into 50 cells each 2 mm wide and each including twenty picture elements. Each line in the register 62 can be clocked in parallel into a store 63 which holds data for a single cell 2 mm square with allowance for overlap between cells. Thus after an initial loading of 21×21 picture elements, each subsequent line filling requires only twenty elements, one element being always retained.

The information to be extracted from each new block of data in store 63 for large-scale and small-scale fault detection comprises:

(1) track area (2) identification of boundary elements and their direction (3) boundary length (4) coordinates of boundary elements.

Once this information has been obtained it can be held separately for the simple arithmetical processing which is involved and the data in store 63 are not retained when the next block is transferred from register 62.

The computation of area simply involves accessing each element of store 63 and using the output to clock a counter which sums all '1's.

Figure 7:
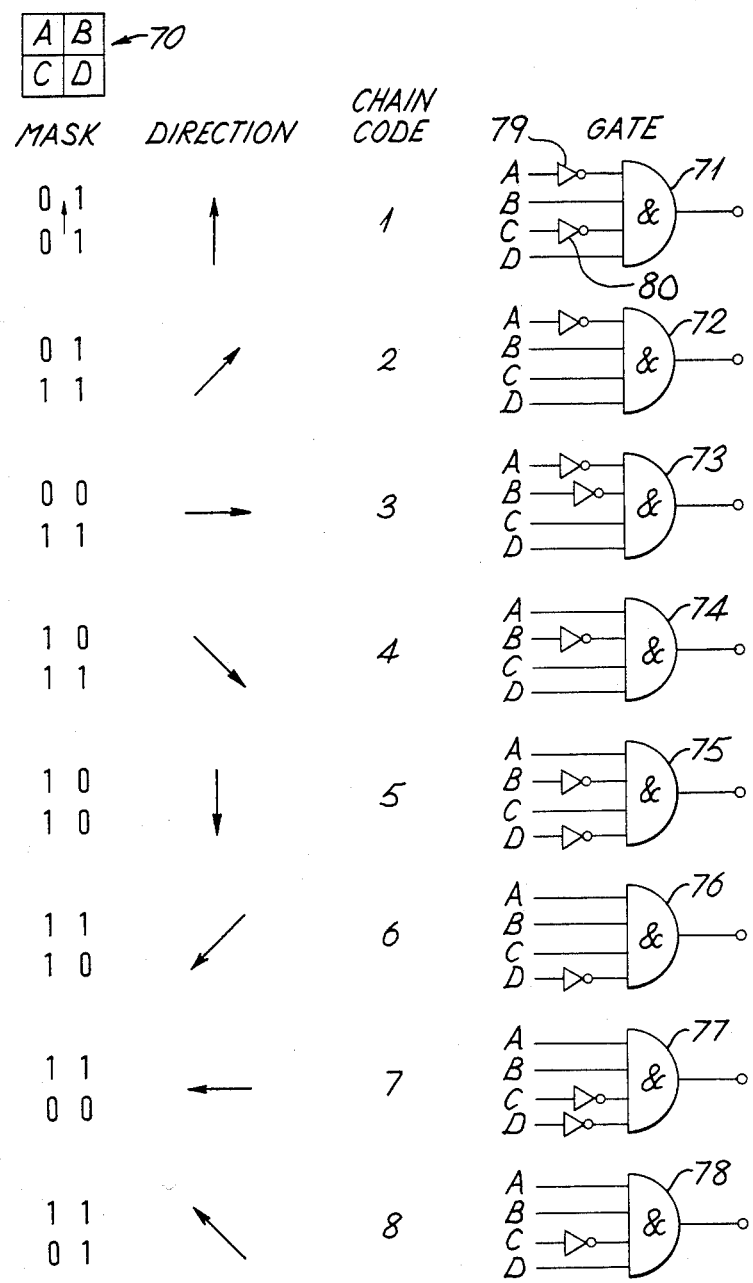
FIG. 7 represents diagrammatically electronic gates for deriving a masked output from data stored in the circuit of FIG. 6.

Identification of the boundary is carrid out by a masking operation in which the contents of store 63 are accessed in sequential, overlapping blocks of four elements. Referring to FIG. 7 a mask 70 labels each element of a block by the letter arrangement:

The status of each element is input to a parallel array of AND gates 71 to 78, each producing an output only in the presence of a respective one of the edge conditions (or mask matching patterns) shown in FIG. 5(b). The edge condition and the associated direction and chain coding are repeated in FIG. 7 for each of the gates 71 to 78 which are hardware embodiments of masks M1 to M8. For example the condition for chain coding '1' which represents an edge directed to the North requires

A=0, C=0, B=1, D=1

Gate 71 is arranged to produce an output for this condition by having direct inputs B and D and inputs A and C inverted by inverters 79, 80. Each other gate is arranged to respond to its assigned input pattern by inverting appropriate inputs. Whenever a block of four elements is accessed which represents a substrate or track remote from an edge, it comprises only '1's or '0's and all gates will remain at zero output.

The outputs from gates 71 to 78 also enable the length of a boundary to be calculated. All boundary elements lying vertically or horizontally (i.e. codes 1, 3, 5, 7) must be of unit length (in terms of the size of the picture element) so that each output from any of gates 71, 73, 75, 77 is arranged to produce a unit increment on a length counter. All diagonal elements must be of length $\sqrt{2}$ elements so that each output from any of gates 72, 74, 76, 78 is arranged to produce an increment of $\sqrt{2}$.

The final requirement is to follow the changes of coordinates along a boundary to enable the calculation of direct distances between two remote points whose separation along the boundary is known. The process of following a boundary is of course indirect. The masking operation proceeds by scanning the contents of store 63 with the set of masks M1 to M8. A boundary other than a horizontal one is thus detected element by element during successive scans and the connecting points between adjoining elements must be recognized in order to build up a continuous boundary. The final data are in the form of a stored sequence of start and finish coordinates for each element. To establish a convention for the handling of coordinate data, FIG. 8(a) represents in an XY system a block of four values in store 63 centred at points LMNP respectively. In general L and N are at $x_o$ and M and P are at $(x_o+1)$; N and P are at yo and L and M are at (yo+1). For simplicity the origin is set at xoyo so that we have N(0,0), P(1,0), L(0,1), M(1,1). A block LMNP which satisfies mask M1 must include a boundary element which is vertical (chain code 1), the start coordinate being (1,0) and the finish coordinate (1,1). FIG. 8(b) is a table of the start and finish points for the boundary elements matching masks M1 to M8. An output from one of the gates 71 to 78 thus denotes the relevant start and finish coordinates with respect to the point N(0,0) which in turn can be related to the full coordinate frame. By reference to FIG. 8(b) it will be seen that masks and corresponding coordinates can be grouped as follows for the cases where an increment occurs and according to the axis on which it occurs.

|  | START | | FINISH | |
|---|---|---|---|---|
|  | X | Y | X | Y |
| M 1,6,7,8 | 1 | | | |
| M 4,5,6,7 | | 1 | | |
| M 1,2,3,4 | | | 1 | |
| M 1,2,7,8 | | | | 1 |

Figure 8C:
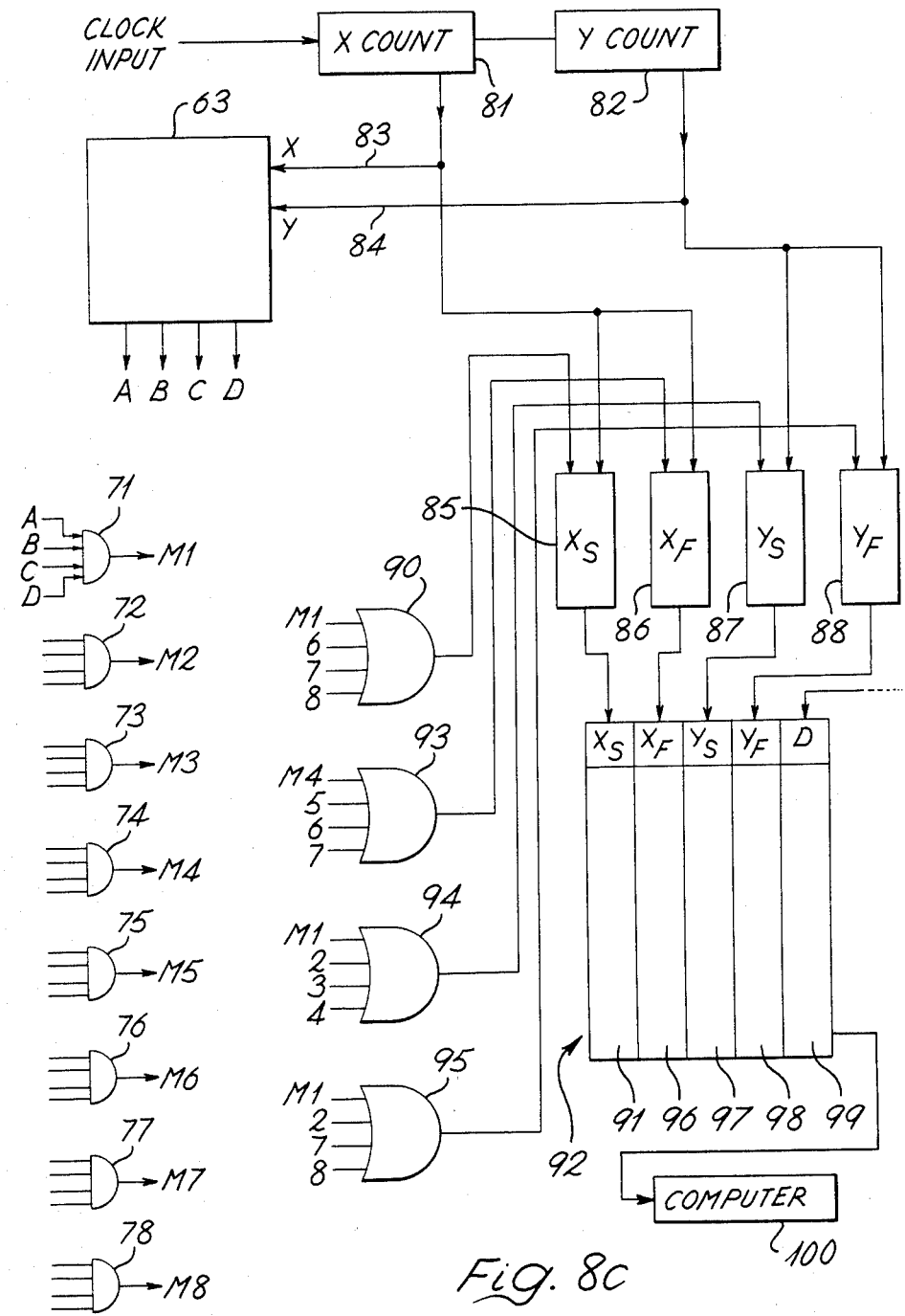
FIG. 8(c) is a block diagram of a circuit for deriving boundary coordinate data from data stored in the circuit of FIG. 6.

With reference to FIG. 8(c) it can now be shown how the local increment is related to the coordinate system of store 63 during mask scanning.

In FIG. 8(c) scanning of store 63 is controlled by a clock input to an X counter 81 and a Y counter 82 having sufficient capacity to count the full number of elements of the camera array in the X and Y directions, respectively. Store 63 is scanned along each line e.g. through points 0-20 by a 5-bit X-count input on an address line 83 and is stepped from line to line by a 5-bit Y-count input on an address line 84. (Only a single line output from counters 81, 82 is shown to represent the 5-bit outputs). The full X-count representing the full X coordinate of each array element is input (i) to an adder 85 from which the X coordinate at the start point of each boundary element is derived and (ii) to a similar adder 86 from which the X coordinate at the finish point of each boundary element is derived. The full Y count is input to corresponding adders 87 (Y state), 88 (Y finish). The mask scanning of store 63 produces outputs on lines ABCD which represent instantaneously the state of each element of the masked block of four elements. At that instant the input counts to counters 85–88 represent the coordinates of the reference epoint (0,0) of FIG. 8(a). As has been explained with reference to FIG. 7 the outputs from store 63 on lines ABCD are tested for the presence of a boundary element and its direction by inputting to gates 71-78, an output from one of which indicates a match with one of masks M1 to M8. The mask outputs and the corresponding coordinate increments can be grouped as noted in a preceding paragraph. Thus, a signal produced by gating an M1 or M6 or M7 or M8 output at an OR gate 90 must represent an increment in the X start coordinate. The output from OR gate 90 is therefore connected to a second input point to adder 85. In the presence of both inputs adder 85 produces an output representing the incremented X start coordinate which equals the curent X count plus one. This value is entered in an X-start column 91 of a store 92. In a similar manner M4,5,6 or 7 inputs to an OR gate 93 produce an incremented output at Y-start adder 87; M1,2,3,4 inputs to an OR gate 94 increment X-finish adder 86; and M1,2,7,8 inputs to an OR gate 95 increment Y-finish adder 88. The outputs from adders 86, 87, 88 are entered in corresponding columns 96,97, 98 of store 92. The directional code is entered in column 99 of store 92 by conversion from the outputs of gates 71-78. Each row of store 92 thus contains all the data on a single boundary element but the entries are generated in the order in which the elements are encountered during scanning. The final operation of assembling sequential data on a complete length of boundary involves scanning store 92 to identify pairs of elements for which the start-coordinates of one element coincide with the finish-coordinates of the other element. Once the chain is assembled with the relevant direction codes, the distances between any chosen points can be calculated and curvature codes derived to apply the defect detection criteria.

The calculation of direct distance between remote start and finish points is the only one requiring arithmetic processes other than addition and subtraction. The additional time in computation which this would involve can be avoided by providing a look-up table of results since the input range of X and Y increments will not be large. In the first stage of small-scale detection for example the increment will not exceed seven.

The provision of hardware for the functions described with reference to FIGS. 6, 7 and 8 enables the inspection programme to be carried out under the control of a suitable microprocessor with auxiliary memory together shown as a computer 100 in FIG. 8(c). A bit slice microprocessor such as that commercially identified as the Advanced Micro Devices 2900 is an example of a suitable device.

The store 92 is scanned by the computer 100 to derive the chain codes of Table I and indicate faults. FIGS. 9(a) to 11(b) show flowcharts for the program held by the computer 100. As will be clear to programmers, programs may be written from the flowcharts which are presented in this form so that any convenient program language can be used.

In an operation 101 of FIG. 9(a) each segment is read in turn from the store 92 and tested at 104 to determine whether it should be linked to the end of an existing chain n. In the test 104 the start coordinates $X_s$ and $Y_s$ of the segment are compared with the end coordinates $X_{fn}$ and $Y_{fn}$ of each of n chains already stored (see operation 108 below). If both respective coordinates satisfy test 104 an operation 105 is carried out in which the current segment is linked to the end of the nth chain by changing the finish coordinates to the finish coordinates of the current segment.

If no chains are found with ends suitable for linking to the current segment, a test 106 is carried out in which the finish coordinates of the segment are compared with the start coordinates of each stored chain and if a match is found the segment is linked in an operation 107 to the start of the matched chain by altering the stored start coordinates to the start coordinates of the segment.

If no chains are found which can be extended by the segment then a new chain is stored in the operation 108 in which the coordinates held by the columns 91 and 96 to 98 and the direction held by column 99 of the store 92 are stored and labelled as a new chain.

After each of operations 103, 105, 107 and 108 a test 110 is carried out to determine whether all the segments of the current cell have been read from the store 92. If not a loop 111 is followed and the next segment is read out in the operation 101.

Figure 9B:
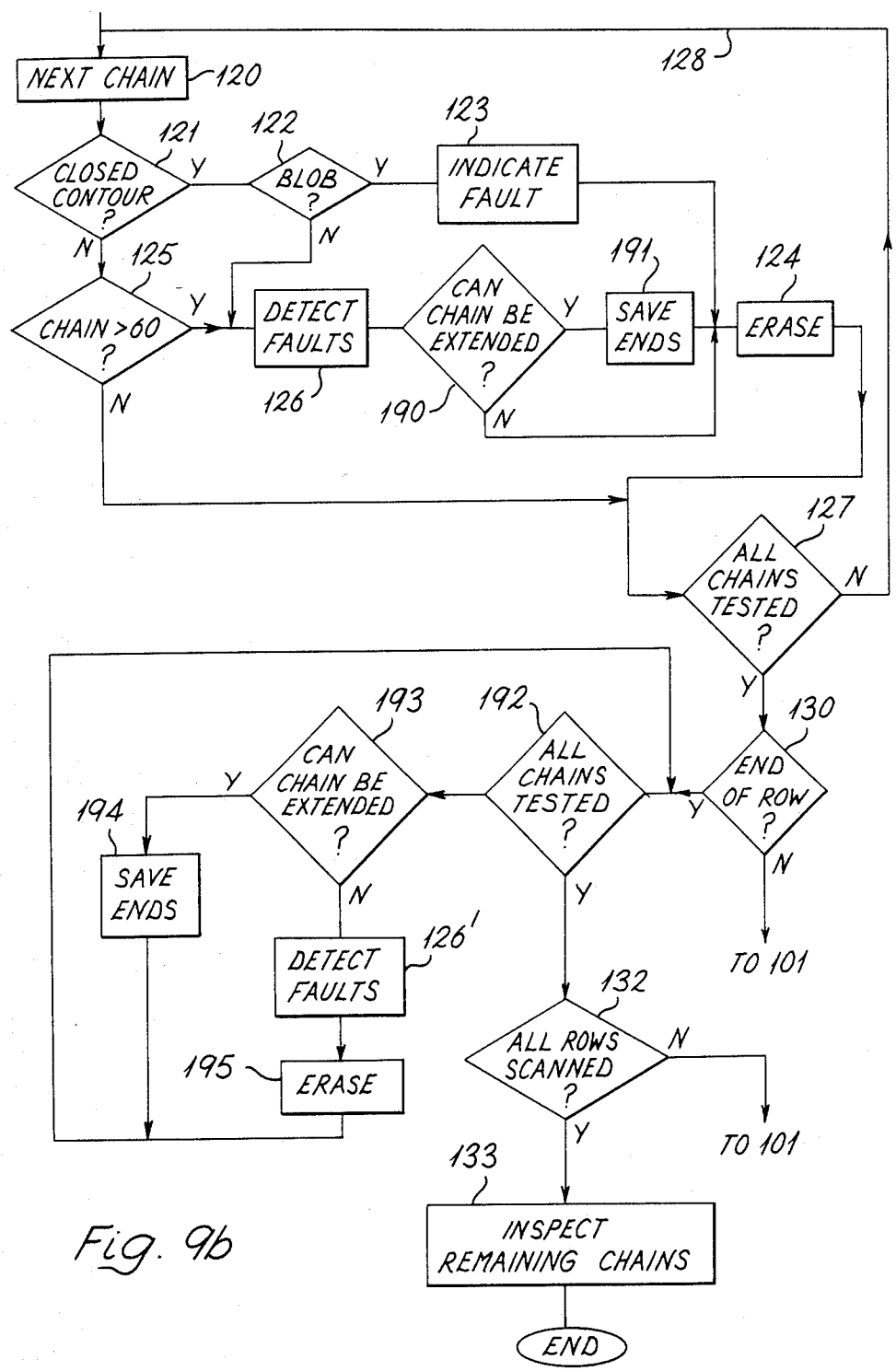
FIG. 9b is a flow chart for testing boundaries for faults.

In the next part of FIG. 9(a) each chain is examined in turn to determine whether it should be linked to another chain, thus linking chains from cell to cell. Thus in repeating an operation 112 each chain is examined in turn and tested in operation 113 to determine whether it should be linked to any other chain. This procedure is the same as that carried out in operations 104 and 106 but if it is discovered in a test 114 that the combined length of a chain would be greater than, typically, 100 chain elements (limited by the amount of storage available), then an operation 115 is carried out in which an overlap of 15 elements is added to the chain being tested. If the test 114 is negative the chains are linked in an operation 116 which is the same as the operations 105 and 107. After the test 113 and the operations 115 and 116, a test 117 is carried out to determine whether all chains in the cell have been tested. If so a number of tests shown in the first part of a flowchart shown in FIG. 9(b) is carried out on all chains. Each chain is selected in an operation 120 and tested (121) to see whether it forms a closed contour by determining whether its respective X and Y start and finish coordinates are equal. If the chain code does described a closed contour a test 122 is carried out to determine whether the number of elements is less than 40 and whether the closed contour corresponds with a known feature on the master pattern. If so a fault is indicated in an operation 123 in a way which will be described later in connection with an operation 173 of FIG. 11(b) and, this chain having been processed, it is erased in an operation 124 to give additional storage room in the computer. The erase operation 124 saves 15 chain elements which abut an edge of a cell which has not yet been processed, thus allowing chains to be extended from cell to cell.

A chain is only tested for faults if it is greater than 60 elements in length and thus a test 125 causes a detect fault routine, to be described later, to be carried out in an operation 126 if the test 125 is satisfied. After fault detection a test 190 is carried out to determine whether the chain can be extended into another cell and if so the either or both ends are stored in an operation 191. For this purpose 15 elements are stored. Should the chain be less than 60 elements, a jump occurs from the test 125 to a test 127 which determines whether there are any more chains in a cell to be tested for faults. If so a loop 128 back to an operation 120 is followed. If not a test 130 is carried out to determine whether the cell being processed for chain codes is at the end of a row in scanning and if not the operation 101 of FIG. 9(a) and following operations are repeated.

If the end of a row has been reached then each remaining chain is tested (193) to determine whether it abuts the lower edge of the last row of cells scanned. If so, an operation 194 saves the last 15 elements of either or both ends of the chain. If the test 193 is negative a detect fault operation 126' which is the same as the operation 126 is carried out and then the chain is erased in an operation 195.

A test 132 is then carried out to determine whether all rows have been scanned and if not a loop back to operation 101 of FIG. 9(a) is followed. Having scanned the last row there may be some portions less than 60 elements of chains remaining and these are tested in operation 133 for blobs and other faults as in operations 122, 123 and 126.

Figure 10:
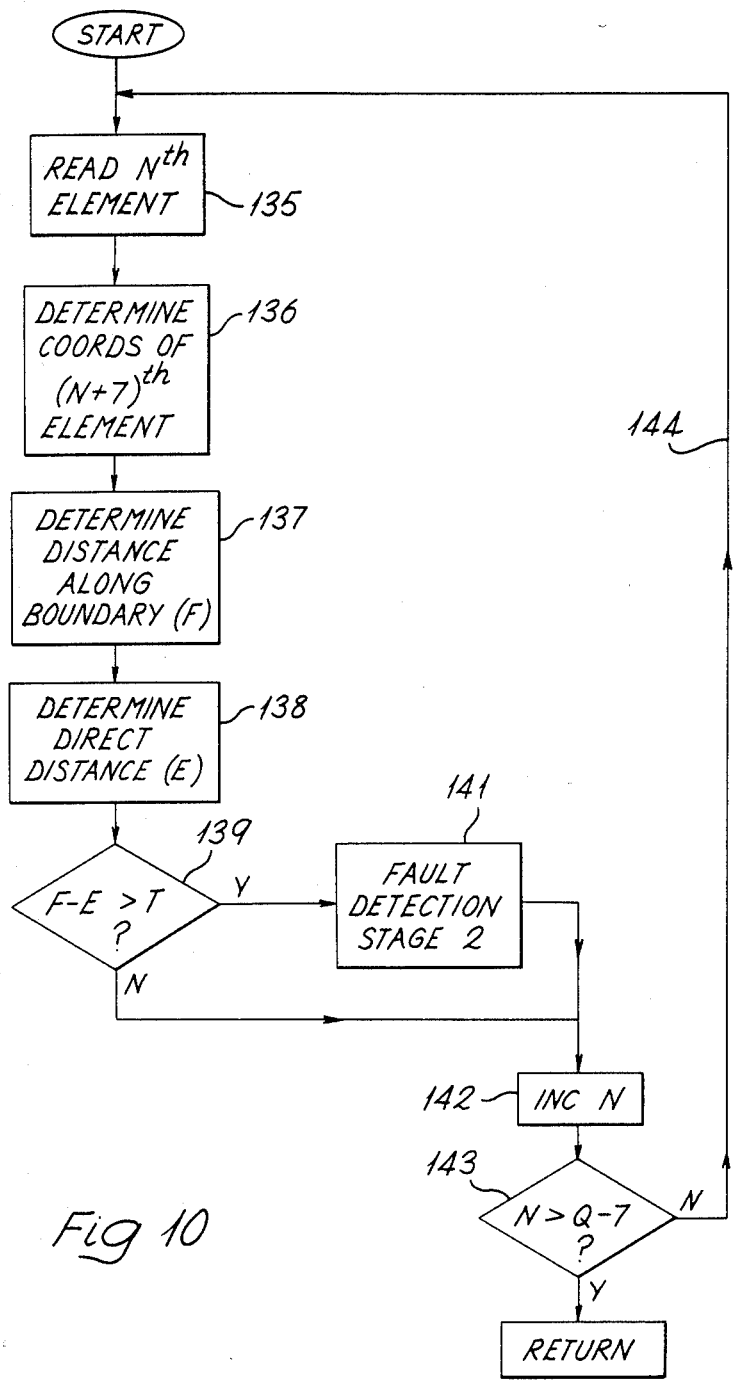
FIG. 10 is a flow chart forming part of the chart of FIG. 9b for carrying out a first stage of fault detection.

The operation 126 of FIG. 9(b) (which is the same as the operation 126') is now explained firstly with reference to FIG. 10 where each of N chain segments making up the current chain is processed in turn. Each element is first read in an operation 135 and then the coordinates of an element spaced by 7 elements from the first element are determined in an operation 136. In order to make this determination the direction codes of each of the seven next elements are considered and the X coordinate of the Nth element held in operation 135 is incremented by one for each element which is in directions 2, 3 and 4 and decremented by one for each element which is in directions 6, 7 and 8. Similarly in order to find the Y coordinate the Y coordinate of the Nth element is incremented by one for each of the next seven elements which has a direction code 4, 5 and 6 and decremented by one for each element which has a direction code 1, 2 and 8.

The distance F along the boundary between the Nth element and the N plus 7th element is now calculated in an operation 137 according to the equation $$F = n + m\sqrt{2}$$

where n is the number of occurrences of directions 1, 3, 5 and 7 in the seven elements from N to (N+7) and m is the number of occurrences of directions 2, 4, 6 and 8 in the same seven elements. In an operation 138 the direct distance between the Nth element and the (N+7)th element is determined by the equation $$E = \sqrt{(X_2 - X_1)^2 + (Y_2 - Y_1)^2}$$

where $X_1$ and $Y_1$ are the coordinates the Nth element and $X_2$ and $Y_2$ are the coordinates of the (N+7)th element.

A test 139 determines whether the difference between the distance along the boundary and the direct distance is greater than the threshold T mentioned above. If so the next stage of fault detection which is described below is carried out in an operation 141 but if not, or after the operation 141, N is incremented by one (operation 142) and then tested to determine whether there are more than seven elements left in the chain (test 143), the chain having a length of Q elements. If not a loop 144 back to the operation 135 is followed so that the test can be carried out for the next element in the chain. If the test 143 is positive a return occurs to operation 124 of FIG. 9(b).

Figure 11A:
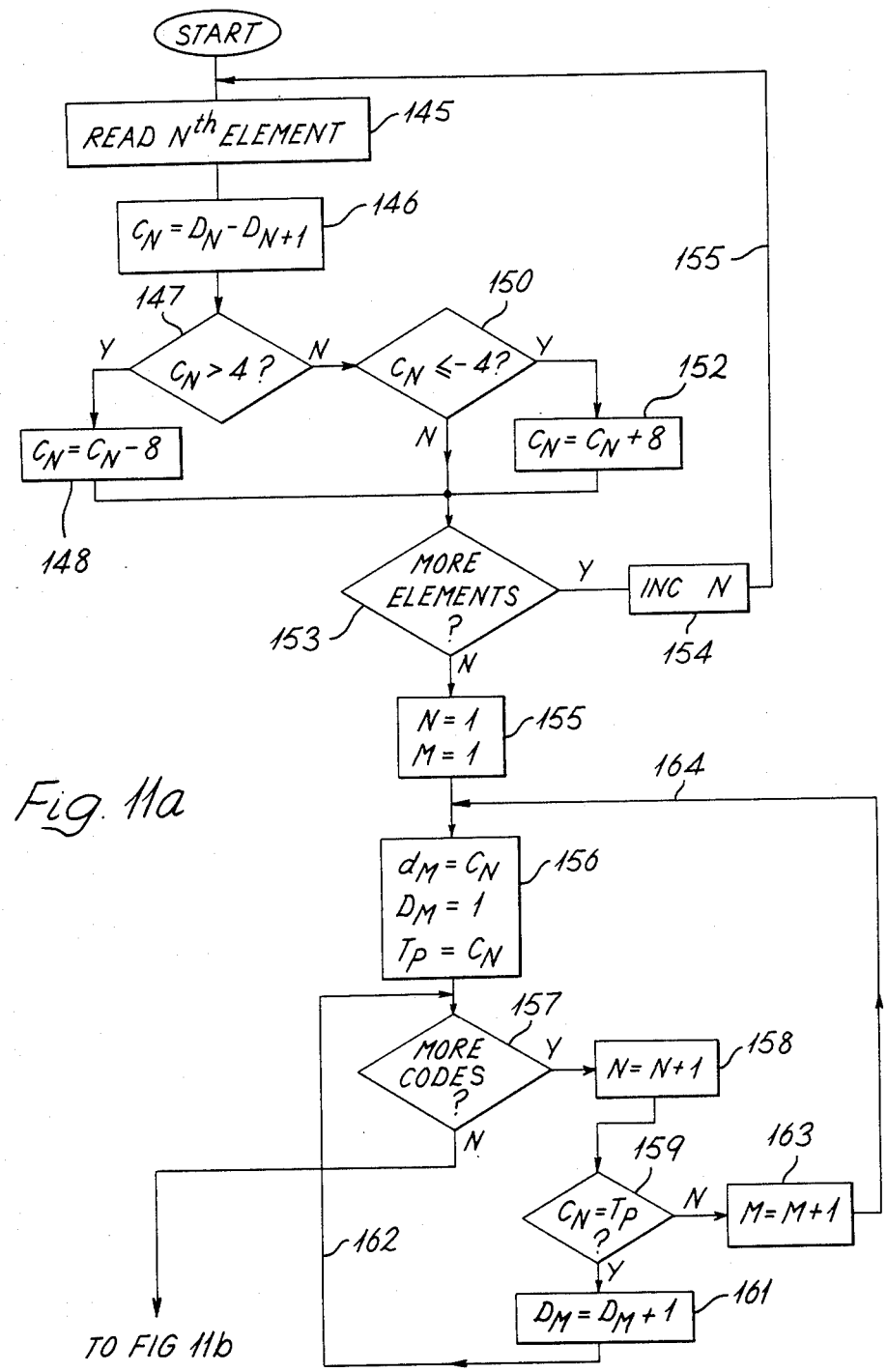
FIG. 11a is a flow chart for deriving curvature codes used in a second stage of fault detection.
Figure 11B:
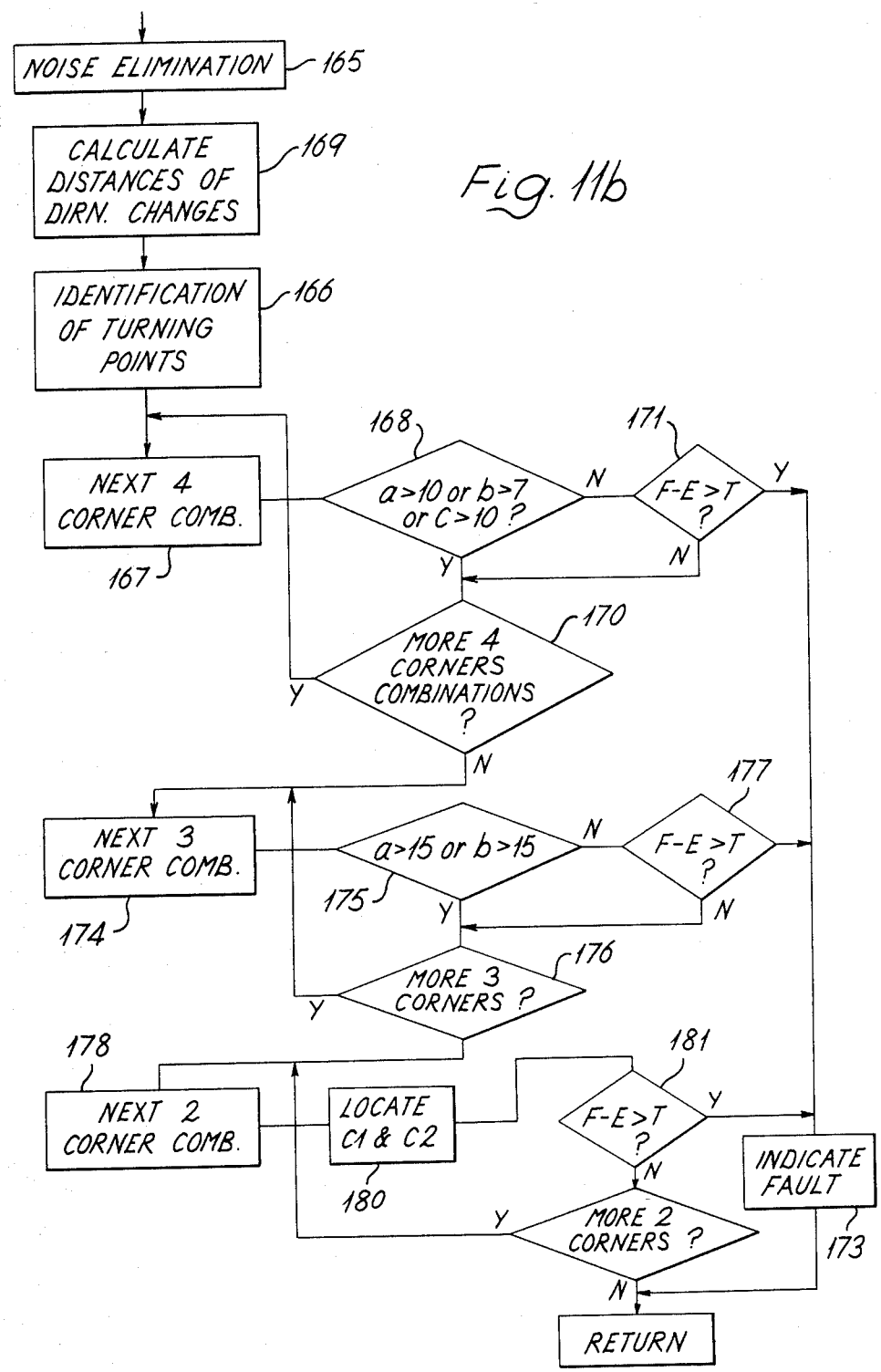
FIG. 11b is a flow chart for carrying out the second stage of fault detection.

Should the first stage of fault detection as described in relation to FIG. 10 indicate the possibility of a fault then the operation 141 now described with reference to FIGS. 11(a) and 11(b) is carried out. First the curvature codes, changes in direction, and durations of Tables I and II are derived. Each of the N elements of a current chain is first considered in a series of operations 145. For each Nth element the difference between the direction code of the Nth element and the direction code of the (N+1)th element is found in an operation 146 to determine a curvature code $C_N$. If this code is greater than 4 as determined by a test 147, eight is subtracted (operation 148). If a test 150 indicates that $C_N$ is less than or equal to $-4$ then an operation 152 adds eight to $C_N$ this is in order to restrict the range of $C_N$ to $-3$ to 4. Following operations 148 and 152 and the test 150 a test 153 is carried out to determine whether there are more elements in the chain. If so N is incremented in operation 154 and the next element in the chain is considered by following loop 155.

If there are no more elements in the chain then arrays $d_M$, $D_M$ and $P_M$ are derived. This derivation is carried out in the second part of FIG. 11(a), $d_M$ giving changes in direction corresponding to column 2 of Table II; $D_M$ gives the duration of each change of direction (column 3 of Table II) and $P_M$ corresponds to distance (last column of Table II but for all changes of direction).

In an operation 155 variables N and M are set to one in an operation 156, $d_1$ is set to the first contour code $C_1$, the duration $D_1$ is set to one, and a variable $T_P$ corresponding to the type of change in direction is set to $C_1$. A test 157 is then carried out to determine whether there are any more codes corresponding to the current chain and if so N is incremented in an operation 158. A test 159 determines whether there is a change in the curvature code as the next element corresponding to the new value of N is considered. If there is no change in curvature code then an operation 161 is carried out to increment the duration $D_M$. A loop 162 back to th test 157 is then followed and the operation 158 is carried out cyclically until a change in curvature code is detected by the test 159 when an operation 163 is carried out to increment M and follow a loop 164, thus initiating new elements in the arrays $d_M$ and $D_M$. When test 157 is negative the second, third and last columns of Table II have been derived and stored in the computer memory and the next stage of operations as shown in FIG. 11(b) is carried out.

The changes of direction column in Table II may contain direction changes which are regarded as "noise" and this noise is eliminated in an operation 165 according to Table III below.

TABLE III

|  | OLD |  | NEW |  | OLD |  | NEW |  | OLD |  | NEW |  |
|---|---|---|---|---|---|---|---|---|---|---|---|---|
| DIRECTION CHANGES | -1 | 0 | -1 | -2 | 1 | 0 | 1 | 2 | -1 | 2 | -1 | 0 |  |
| DURATION | 1 | 1 | 1 | 3 | 1 | 1 | 1 | 3 | 1 | 1 | 1 | 3 |  |
| DIRECTION CHANGES | 1 | -2 | 1 | 0 | 1 | -1 | 1 | 0 | 1 | 0 | -1 | 1 | -1 | 0 | -1 | 0 |
| DURATION | 1 | 1 | 1 | 3 | 1 | 1 | 1 | 1 | 1 | 1 | 1 | 1 | 1 | 1 | 1 | 1 |
| DIRECTION CHANGES | 1 | -1 | 0 | -1 | 1 | 0 |  |
| DURATION | 1 | 1 | 2 | 1 | 1 | 2 |  |

In each section of Table III a sequence of two or three direction changes as shown occurring within a duration of two or three, respectively, chain code elements are replaced by the changes in direction changes and duration shown.

Having removed noise, the distances of each turning point from the start of the divergence are calculated in an operation 169 from the equation:

$$P_m = \left[ \sum_{n=1}^{m-1} D_m \right] + \frac{D_m}{2}$$

Turning points in the chain code are now determined where a direction change is less than or equal to $-1$ or greater than or equal to $+1$ and each turning point is held in computer store together with the corresponding variable P (operation 166).

Figure 12A:
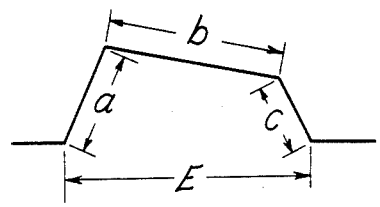
FIG. 12(a) illustrates a four corner boundary divergence in a track.

Sequence of turning points as now stored may indicate faults in the form of boundary divergences. Each divergence having 4, 3 or 2 corners is now examined in order to confirm the possible fault so far detected. In an operation 167 sequences of signs having the form $+*-*-*+$ or $-*+*+*-$ are identified as indicating a four corner divergence (where an asterisk denotes the possible occurrence of a sign which can be either plus or minus). For each such sequence a test 168 is carried out to determine whether lengths a, b and c in terms of chain code segments are greater than 10, 7 and 10 elements respectively (a, b and c are as shown in FIG. 12a). If any of a, b or c is greater than its respective limit no fault is present and the next combination of four corners is considered following a test 170. If the test 168 is satisfied a further test 171 is carried out to determine whether the difference between the distance (F) along the boundary and the direct distance (E) between the initial corners of the boundary is greater than a threshold of 2.3; where F=a+b+c and E is determined from the equation given above but with $X_1 Y_1$ and $X_2 Y_2$ relating to the points at the beginning and end of the divergence. If the test 168 fails a return is made by way of the test 170 to the operation 167, but if not, an operation 173 takes place when an indication of a fault is given. This indication can be in many forms, for example by printing out the coordinates of the fault or by marking the fault on a display of the pattern sensed, this pattern being available for display in the form of the boundaries determined as described.

Figure 12B:
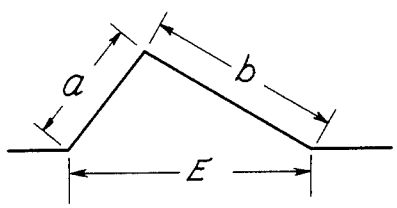
FIG. 12(b) illustrates a three corner boundary divergence in a track.
Figure 12C:
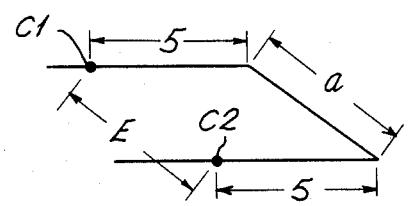
FIG. 12(c) illustrates a two corner boundary divergence in a track.

After all four corner combinations have been checked the test 170 leads to an operation 174 in which all three corner combinations "$+*-*+$" or "−*+*−" in the changes of direction code corresponding to a chain are tested. If according to a test 175 a or b are greater than 15 where a and b are as shown in FIG. 12(b) then the next three corner combination is considered in the operation 174 after a test 176 has been carried out. If the test 175 suggests a fault may be present a test 177 is carried out to determine whether F−E is greater than T where F=a+b and E is as shown in FIG. 12(b) and T is again 2.3. If test 177 is satisfied then a fault indication is given in the operation 173.

When the test 176 indicates that all three corner combinations have been processed the first two corner combination, that is "+*+" or "−*−" is located in an operation 178 and two points C1 and C2 on the chain code five segments from the corners are located in an operation 180. Then a test 181 to determine whether F−E is greater than a threshold is carried out where F=a+10, E is the direct distance between points C1 and C2 and T is 8.0. A typical two corner fault is as shown in FIG. 2(e).

After indicating a fault or on coming to the end of the two corner combinations a return to the operation 142 of FIG. 10 occurs. Since this operation itself represents the operation 126 or 126' of FIG. 9(b), all chains are eventually inspected for faults and the board inspection is completed.

A further stage of fault detection which is now described may be desirable in some circumstances. The object is to compare the depth of a reentrant divergence with the width of a conducting track. This further stage may be inserted twice in the flow chart of FIG. 11b to follow each of tests 171 and 177 with a possible return to tests 170 and 176 respectively.

Figure 12D:
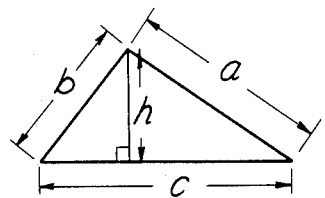
FIG. 12(d) illustrates dimensions used in testing a three corner divergence in a track.
Figure 13:
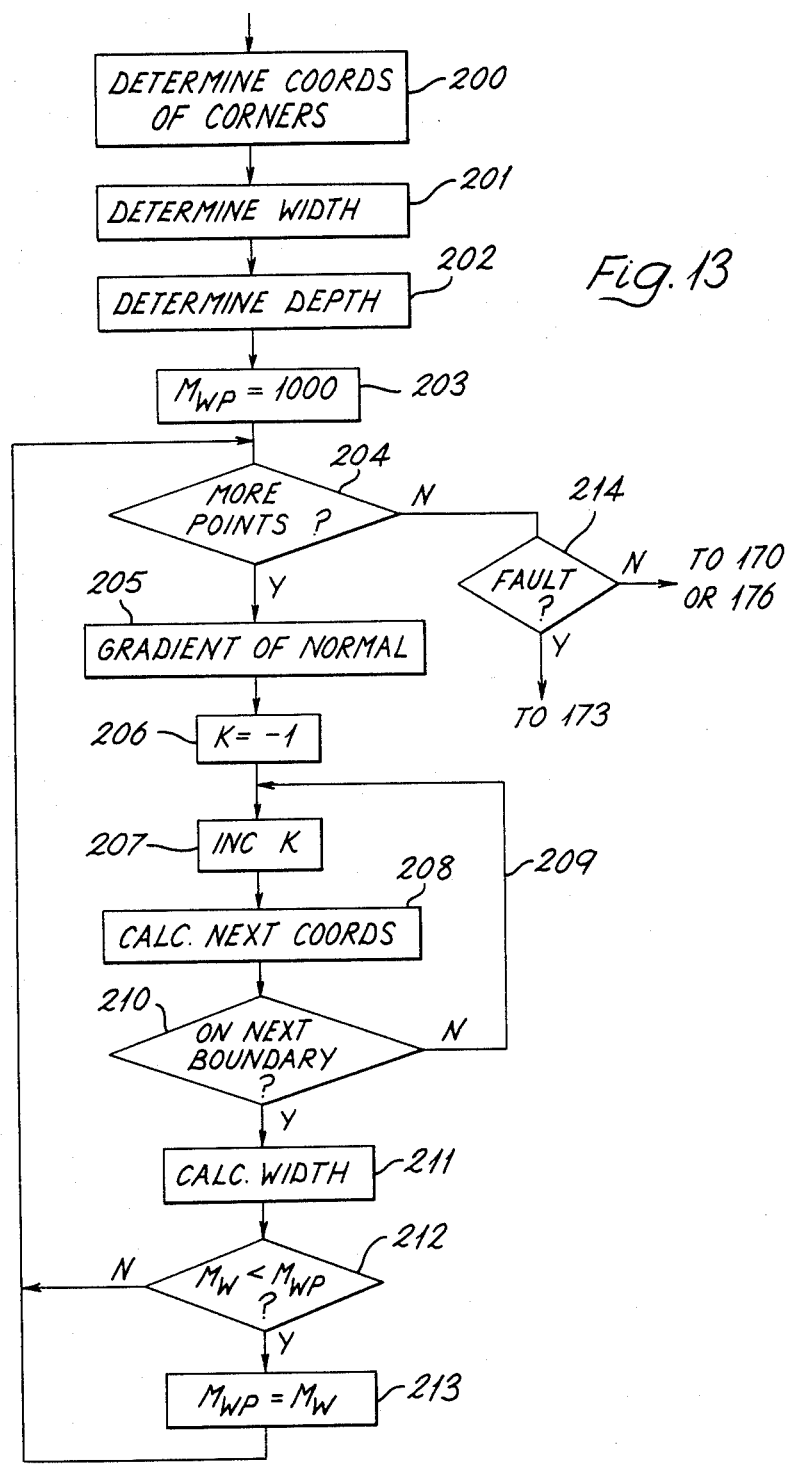
FIG. 13 is a flow chart of a further stage of fault detection.

The further stage is shown in FIG. 13 where the coordinates of the corners of the divergence are first determined in an operation 200 using the relevant value of $P_M$ and the same type of technique as described in connection with the operation 136. The width of the fault is then determined from these coordinates in an operation 201 and its depth $D_F$ in an operation 202 from the equations $$d=(b^2+c^2-a^2)/2c$$

$$h=D_F=(b^2-d^2)^{\frac{1}{2}}$$

where a, b, c, d, h are as shown in FIG. 12d.

A series of operations is now carried out to determine the minimum distance across the track from the reentrant and this is obtained by finding the lengths of a number of normals at points along the reentrant to the adjacent boundary and selecting the shortest normal as the required minimum distance. Normals are found for every pair of successive elements in the reentrant and every pair of elements spaced by one element.

First a variable $M_{WP}$ is set to 1,000 in an operation 203 and then a test (204) is carried out to determine whether every pair of points has been tested. For each pair of points the gradient of the normal to the line joining these points is determined in an operation 205 by taking the negative inverse of the gradient of the line joining the points. Next a variable K is set to −1 and then incremented by 1 in operations 206 and 207. The coordinates of the next point in the normal are then calculated from the following equations $$x_N = x_1 + \frac{(x_2 - x_1)}{H} K$$

-continued $$y_n = y_1 + \frac{(y_2 - y_1)}{H} K$$

$$H = \sqrt{(x_2 - x_1)^2 + (y_2 - y_1)^2}$$

where $x_1$, $y_1$ and $x_2$, $y_2$ are the coordinates of the pairs of points in the boundary and $x_N$, $y_N$ are the next point in the normal. A test 210 determines whether the next boundary has been reached from data already stored, relating to whether a point is on a conducting path or not. If not a jump 211 back to the point where K is incremented is carried out but if the next boundary has been reached then the length ($M_W$) of the normal is calculated in an operation 211 from the coordinates of the end points of the normal. A test 212 determines whether the new length $M_W$ is less than the previously stored value and if so the new value is stored as $M_{WP}$ in an operation 213.

After all pairs of points in the boundary have been considered a test 214 is carried out to determine if $$\frac{D_F}{D_F + M_{WP}} > 20\%$$

If the test 214 is satisfied then the fault indication is given in the operation 173 of FIG. 11b but if not there is a return to test 170 or 176 as appropriate.

The choice of parameters in carrying out the invention will depend on the nature of the workpiece and the characteristics of the pattern, but is also governed by the overall inspection strategy.

In particular if the procedure described herein is used for the detection of both large-scale and small-scale defects the initial sensing signal is common and the sensitivities of the subsequent processing stages can be chosen by setting the parameters so that the ranges of large-scale detection and small-scale detection will overlap. There is then a minimum probability that any defect of intermediate size will fall undetected between the ranges.

Such variables as the size of the cell 12 (FIG. 1) and the threshold level at which a boundary deviation is to be recognised as a defect must be determined by the user and may then be input by him for storage in unit 36.

A different automatic system, or visual inspection, may of course be used for large-scale detection in conjunction with the small-scale detection system of the invention, but the risk must then be considered that the ranges of sensitivity will not overlap.

The invention has been described specifically in relation to the inspection of printed circuits of a particular scale of construction. In a circuit in which the track width, for example, is much smaller than 1 mm the scale of measurement described for defect detection must be reduced accordingly. It is also intended that the invention should be applicable to other kinds of pattern in which boundaries can be distinguished having a characteristic regularity, a deviation from which is significant of the quality of the workpiece.

We claim:

1. A method of detecting anomalies in a reproduction of a pattern on a workpiece comprising the operation of irradiating that surface of the workpiece carrying the pattern, scanning the said surface with detection means sensitive to such radiation to derive a video signal representing an array of points on the said surface, the signal having at least two levels relating to respective features of the pattern, deriving a digital value of the signal for each point, comparing each such value with a predetermined threshold value to determine those points which constitute a first feature of the pattern, determining those points which define a boundary of the first feature, determining changes of direction between successive points on the boundary, and using the changes in direction so determined to identify any anomaly in the boundary which has at least one dimension which is comparable to the smallest dimension of the pattern.

2. A method according to claim 1 wherein an identification of an anomaly in the boundary is made at least partially by comparing the length of the boundary between two separated points in the boundary with the direct distance between the points.

3. A method according to claim 2 wherein the comparison is made at progressively displaced positions on the boundary, each pair of points being separated by an equal number of boundary elements.

4. A method according to claim 1 wherein an identification of an anomaly is made, at least partially, by identifying any sequence of changes of direction which indicate a divergence in the boundary which is comparable to the smallest dimension of the pattern.

5. A method according to claim 1 wherein an identification of an anomaly is made at least partially if a sequence of changes in direction of the boundary includes two changes in the same sense separated by at least one change of the opposite sense.

6. A method according to claim 1 including the following steps for identifying large-scale faults: positioning the workpiece in a predetermined orientation for scanning, deriving values of parameters for elemental areas forming the said surface and comparing with values for corresponding elemental areas of a master pattern, the parameters being the perimeter length of the first feature of the pattern and the area of the feature.

7. A method according to claim 1 wherein an identification of an anomaly is made at least partially by determining the ratio of the depth of a reentrant in the boundary divided by the sum of the depth of the reentrant and the minimum distance at the reentrant between the boundary and another boundary joined thereto by the said first feature, and comparing the ratio with a predetermined limit.

8. Apparatus for detecting anomalies in a reproduction of a pattern on the surface of a workpiece comprising means for irradiating the said surface such that at least two different levels of reflectance relate to respective features of the pattern, means responsive to such reflected radiation for scanning the said surface to derive a video signal representing the reflectance at each of an array of points on the surface, means for deriving a digital value of the signal for each point, means for comparing each value with a predetermined threshold value to determine those points which represent a first feature of the pattern, means for identifying those points which define boundaries of the first feature, means for deriving the directions of the boundaries between points, and means for analysing the said directions to indicate the presence of anomalies in the boundaries which have at least one dimension which is comparable to the smallest dimension of the pattern.

9. A method of detecting anomalies in a reproduction of a pattern on a workpiece comprising the operation of irradiating that surface of the workpiece carrying the pattern, scanning the said surface with detection means sensitive to such radiation to derive a video signal representing an array of points on the said surface, the signal having at least two levels relating to respective features of the pattern, deriving a digital value of the signal for each point, comparing each such value with a predetermined threshold value to determine those points which constitute a first feature of the pattern, determining those points which define a boundary of the first feature, determining changes of direction between successive points on the boundary, and identifying any anomaly in the boundary, which has at least one dimension which is comparable to the smallest dimension of the pattern, at least partially by comparing the length of the boundary between two separated points in the boundary with the direct distance between the points.

10. A method according to claim 9 wherein the comparison is made at progressively displaced positions on the boundary, each pair of points being separated by an equal number of boundary elements.

11. A method of detecting anomalies in a reproduction of a pattern on a workpiece comprising the operation of irradiating that surface of the workpiece carrying the pattern, scanning the said surface with detection means sensitive to such radiation to derive a video signal representing an array of points on the said surface. the signal having at least two levels relating to respective features of the pattern, deriving a digital value of the signal for each point, comparing each such value with a predetermined threshold value to determine those points which constitute a first feature of the pattern, determining those points which define a boundary of the first feature, determining changes of direction between successive points on the boundary, and identifying any anomaly in the boundary, which has at least one dimension which is comparable to the smallest dimension of the pattern, wherein an identification of an anomaly is made, at least partially, if a sequence of changes in direction of the boundary includes two changes in the same sense separated by at least one change of the opposite sense.

12. A method of detecting anomalies in a reproduction of a pattern on a workpiece comprising the operation of irradiating that surface of the workpiece carrying the pattern, scanning the said surface with detection means sensitive to such radiation to derive a video signal representing an array of points on the said surface, the signal having at least two levels relating to respective features of the pattern, deriving a digital value of the signal for each point, comparing each such value with a predetermined threshold value to determine those points which constitute a first feature of the pattern, determining those points which define a boundary of the first feature, determining changes of direction between successive points on the boundary, and identifying any anomaly in the boundary which has at least one dimension which is comparable to the smallest dimension of the pattern, wherein an identification of an anomaly is made, at least partially by determining the ratio of the depth of a reentrant in the boundary divided by the sum of the depth of the reentrant and the minimum distance at the reentrant between the boundary and another boundary joined thereto by the said first feature, and comparing the ratio with a predetermined limit.

13. Apparatus for detecting anomalies in a reproduction of a pattern on the surface of a workpiece comprising means for irradiating the said surface such that at least two different levels of reflectance relate to respective feature of the pattern, means responsive to such reflected radiation for scanning the said surface to derive a video signal representing the reflectance at each of an arry of points on the surface, means for deriving a digital value of the signal for each point, means for comparing each value with a predetermined threshold value to determine those points which represent a first feature of the pattern, means for identifying those points which define boundaries of the first feature, means for deriving the directions of the boundaries between points, and means for analyzing the said directions to indicate the presence of anomalies in the boundaries which have at least one dimension which is comparable to the smallest dimension of the pattern, wherein the means for analyzing the said directions compares the length of each boundary between two separated points in that boundary with the direct distance between the points, the comparison being repeated for a plurality of pairs of points in the boundary.

14. Apparatus for detecting anomalies in a reproduction of a pattern on the surface of a workpiece comprising means for irradiating the said surface such that at least two different levels of reflectance relate to respective features of the pattern, means responsive to such reflected radiation for scanning the said surface to derive a video signal representing the reflectance at each of an array of points on the surface, means for deriving a digital value of the signal for each point, means for comparing each value with a predetermined threshold value to determine those points which represent a first feature of the pattern, means for identifying those points which define boundaries of the first feature, means for deriving the directions of the boundaries between points, and means for analyzing the said directions to indicate the presence of anomalies in the boundaries which have at least one dimension which is comparable to the smallest dimension of the pattern, wherein the means for analyzing the said directions is responsive to anomalous sequential changes in directions of each boundary.

* * * * *